(12) United States Patent
Bruenjes et al.

(10) Patent No.: US 10,093,626 B2
(45) Date of Patent: Oct. 9, 2018

(54) PROCESS FOR PREPARING PIPERIDINE-4-CARBOTHIOAMIDE HYDROCHLORIDE

(71) Applicant: BAYER CROPSCIENCE AKTIENGESELLSCHAFT, Monheim am Rhein (DE)

(72) Inventors: Marco Bruenjes, Hattersheim am Main (DE); Mark James Ford, Wiesbaden-Breckenheim (DE)

(73) Assignee: BAYER CROPSCIENCE AKTIENGESELLSCHAFT, Monheim am Rhein (DE)

(*) Notice: Subject to any disclaimer, the term of this patent is extended or adjusted under 35 U.S.C. 154(b) by 0 days.

(21) Appl. No.: 15/555,861

(22) PCT Filed: Feb. 29, 2016

(86) PCT No.: PCT/EP2016/054193
§ 371 (c)(1),
(2) Date: Sep. 5, 2017

(87) PCT Pub. No.: WO2016/139165
PCT Pub. Date: Sep. 9, 2016

(65) Prior Publication Data
US 2018/0044294 A1 Feb. 15, 2018

(30) Foreign Application Priority Data
Mar. 5, 2015 (EP) ..................................... 15157800

(51) Int. Cl.
*C07D 211/62* (2006.01)
(52) U.S. Cl.
CPC .................. *C07D 211/62* (2013.01)
(58) Field of Classification Search
CPC .................................................. C07D 211/62
USPC ....................................................... 546/245
See application file for complete search history.

(56) References Cited

U.S. PATENT DOCUMENTS

| | | | |
|---|---|---|---|
| 9,790,182 B2 * | 10/2017 | Brunjes | A01N 43/40 |
| 2006/0084808 A1 | 4/2006 | Kauskik et al. | |
| 2009/0156592 A1 | 6/2009 | Pasteris et al. | |
| 2009/0270402 A1 * | 10/2009 | Calderwood | C07D 487/04 514/249 |
| 2010/0240619 A1 | 9/2010 | Vann et al. | |
| 2010/0286147 A1 | 11/2010 | Hanagan et al. | |
| 2011/0313160 A1 * | 12/2011 | Chen | C07D 401/04 544/331 |
| 2013/0030002 A1 | 1/2013 | Hanagan et al. | |
| 2013/0045948 A1 | 2/2013 | Dung et al. | |
| 2015/0031541 A1 | 1/2015 | Lamberth et al. | |
| 2015/0065541 A1 | 3/2015 | Cristau et al. | |
| 2017/0137381 A1 * | 5/2017 | Brunjes | C07D 211/62 |

FOREIGN PATENT DOCUMENTS

| | | |
|---|---|---|
| WO | 2005086700 A2 | 9/2005 |
| WO | 2008013622 A2 | 1/2008 |
| WO | 2009094407 A2 | 7/2009 |
| WO | 2011072207 A1 | 6/2011 |
| WO | 2011076699 A1 | 6/2011 |
| WO | 2011146182 A1 | 11/2011 |
| WO | 2013127808 A1 | 9/2013 |

OTHER PUBLICATIONS

Fisher Scientific 4-Cyanopiperidine MSDS Created Nov. 13, 2011.*
Fisher Scientific 4-Cyanopiperidine hydrochloride MSDS Created Nov. 21, 2013.*
PCT International Search Report for PCT/EP2016/054193, dated Apr. 25, 2016.
Gardner, et al., "Synthesis of Compounds for Chemotherapy of Tuberculosis. VII. Pyridine N-Oxides with Sulfur-Containing Groups," J. Organic Chem., (1957) vol. 22: 984-986.
Kuroyan, et al., "Synthesis of Thiazoles of the Piperidine Series," Armyanskii Khimicheskii Zhurnal/Armenian Chemical Journal, (1983) vol. 36: 610-614.
English English Translation of Kuroyan, et al., "Synthesis of Thiazoles of the Piperidine Series," Armyanskii Khimicheskii Zhurnal/Armenian Chemical Journal, (1983) vol. 36: 610-614.
Raymond Houssin, "Synthesis of Some Spin-labeled Bithiazoles, Useful Probes for Studying Bleomycin-DNA Binding," J. Heterocyclic Chem., (1984) vol. 21: 465-469.

* cited by examiner

*Primary Examiner* — Daniel R Carcanague
(74) *Attorney, Agent, or Firm* — McBee Moore Woodward & Vanik IP, LLC

(57) ABSTRACT

The present invention describes a novel process for preparing piperidine-4-carbothioamide hydrochloride.

20 Claims, No Drawings

PROCESS FOR PREPARING PIPERIDINE-4-CARBOTHIOAMIDE HYDROCHLORIDE

CROSS-REFERENCE TO RELATED APPLICATIONS

This application is a National Stage entry of International Application No. PCT/EP2016/054193, filed Feb. 29, 2016, which claims priority to European Patent Application No. 15157800.2, filed Mar. 5, 2015.

BACKGROUND

Field

The present invention relates to a novel process for preparing piperidine-4-carbothioamide hydrochloride (I).

Description of Related Art

Piperidine-4-carbothioamide derivatives are important precursors for active pharmaceutical and agrochemical ingredients (cf. WO 2008/013622, WO 2011/072207 and WO 2011/076699).

The preparation of 4-cyanopiperidine, as a starting material for the preparation of piperidine-4-carbothioamide, generally proceeds from the piperidine-4-carbamide and is known from various literature references and patents (*J. Org. Chem.* 1957, 22, 984-986; US 2006/0084808). Dewatering, for example by means of phosphorus oxychloride or thionyl chloride, at first gives rise to the corresponding 4-cyanopiperidine hydrochloride which, after neutralization with a suitable base and subsequent extraction, gives access to the free amine (4-cyanopiperidine).

The preparation of piperidine-4-thioamide is again effected with addition of hydrogen sulphide to give the 4-cyanopiperidine. In the known preparation processes for piperidine-4-carbothioamide derivatives by means of hydrogen sulphide, for example in WO 2008/013622 and WO 2011/072207, and also in WO 2011/146182, WO 2009/094407 and US 2010/0240619 among other documents, however, the N-substituted 4-cyanopiperidine starting material is required in all cases, which necessitates an additional synthesis step. An additional disadvantage in these processes is found to be that either stoichiometric use of a base (e.g. diethanolamine) is needed, DMF has to be used as solvent, a dry ice condenser is needed or an aqueous workup (large amounts of waste) has to be done. Alternative bases are used, inter alia, in WO 2011/072207 and in *Armianskii khimicheskiĭ zhurnal* 1983, 36, 610-614 (diethylamine, pyridine and triethylamine); in this case, the hydrogen sulphide may also be used in the form of one of its salts (sodium sulphide, sodium hydrogensulphide, etc.). A further hydrogen sulphide source used may also be ammonium sulphide (which is stable only as an aqueous solution), as, for example, in WO 2013/127808 in the synthesis of a substituted piperidine-4-carbothioamide.

In the only literature-described synthesis of piperidine-4-carbothioamide (see *J. Org. Chem.* 1957, 22, 984-986), the initial charge is a 30% methanolic ammonia solution and the 4-cyanopiperidine, and hydrogen sulphide is finally introduced until saturation is complete. This process too shows the disadvantages already mentioned, for example the additional use of a base (ammonia).

The piperidine-4-thioamide obtained from the 4-cyanopiperidine can be used for a wide variety of purposes, including in the synthesis of thiazole derivatives. In what is called the Hantzsch thiazole synthesis, for this purpose, thioamides are reacted, for example, with chloroacetyl derivatives to give corresponding thiazoles. In the case of some thioamide derivatives, it may be advantageous to choose acidic reaction conditions, for example when one of the co-reactants has a primary or secondary amine as further functional group, the reactivity of which is distinctly lowered as a result of the deliberate protonation, and which thus does not lead to any unwanted, competing side reaction in the thiazole synthesis.

It is therefore desirable to obtain a direct route to piperidine-4-carbothioamide hydrochloride (I) without having to neutralize the 4-cyanopiperidine hydrochloride (II) initially obtained for the subsequent reaction with hydrogen sulphide. The advantage lies in saving of a stoichiometric amount of the base required in each case for the neutralizing operation, and of an additional stoichiometric amount of hydrogen chloride in order to reform the corresponding hydrochloride after the preparation of the piperidine-4-carbothioamide.

In the light of the prior art described above, the problem addressed by the present invention is that of providing a process which does not have the aforementioned disadvantages and hence gives a more direct route to piperidine-4-carbothioamide hydrochloride (I) in high yields.

SUMMARY

The above-described problem has been solved by a process for preparing piperidine-4-carbothioamide hydrochloride of the formula (I)

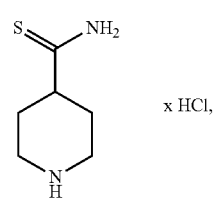

(I)

characterized in that 4-cyanopiperidine hydrochloride of the formula (II)

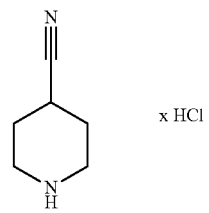

(II)

is reacted with hydrogen sulphide (III) in the presence of a catalytic amount of base of the formula (IV)

$$R^1N(R^2)R^3 \qquad (IV),$$

in which
R$^1$, R$^2$, R$^3$ are each independently hydrogen, C$_1$-C$_{20}$ alkyl, aryl or heteroaryl
or of a catalytic amount of heteroaromatic base from the group of the pyridines (V)
and
of a solvent to give compounds of the formula (I).

DETAILED DESCRIPTION OF A PREFERRED EMBODIMENT

Surprisingly, the piperidine-4-carbothioamide hydrochloride of the formula (I) can be prepared with good yields and in high purity in various solvents with addition only of a catalytic amount of base, which means that the process according to the invention overcomes the abovementioned disadvantages of the preparation processes described in the prior art. This reaction is preferably carried out in a closed reaction vessel.

Process Description

Scheme 1:

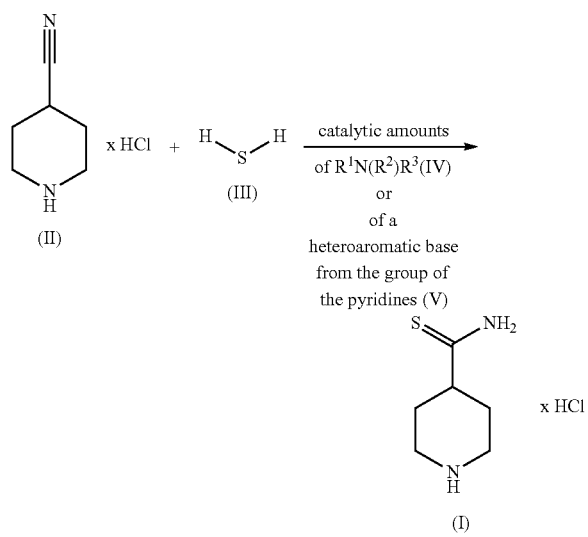

Piperidine-4-carbothioamide hydrochloride (I) is prepared by reacting 4-cyanopiperidine hydrochloride (II) with hydrogen sulphide (III) and a base (IV) or (V) in a catalytic amount in a suitable solvent.

The catalytic amount of the base (IV) or (V) used is typically between 0.1% and 20%, preferably between 1% and 5%, based in each case on the amount of the piperidine-4-carbothioamide hydrochloride (I) used.

Suitable solvents are solvents from the group of the ethers (for example tetrahydrofuran, diethyl ether, methyl tert-butyl ether), aliphatics and aromatics (for example heptane, cyclohexane, benzene, toluene or xylene), alcohols (for example methanol, ethanol, isopropanol, n-butanol, i-butanol, tert-butanol, cyclopentanol, cyclohexanol), amides (for example dimethylformamide, dimethylacetamide), water or else mixtures of these groups of solvents. Preference is given here to alcohols: primary, secondary and tertiary alcohols. Particular preference is given to alcohols having 1 to 10 carbon atoms. Very particular preference is given to methanol, ethanol, isopropanol, n-butanol, i-butanol, cyclohexanol, cyclopentanol. n-Butanol is especially preferable. Methanol is additionally especially preferable. Ethanol is additionally especially preferable. Isopropanol is additionally especially preferable. i-Butanol is additionally especially preferable. Cyclohexanol is additionally especially preferable. Cyclopentanol is additionally especially preferable.

Hydrogen sulphide (III) is introduced into the reaction vessel in gaseous form and the reaction vessel internal pressure is monitored and adjusted to a pressure in a range between 0 and 10 bar (relative pressure). Depending on its solubility in the particular solvent used, it is typically necessary to use hydrogen sulphide (III) at least in an equimolar amount or in excess (1.00 to 10 equivalents, preferably 1.1 to 5 equivalents, more preferably 1.5 to 3 equivalents) based on the compound of formula (II).

Bases used for the reaction according to the invention may be bases of the formula (IV): $R^1N(R^2)R^3$ where $R^1$, $R^2$, $R^3$ are each independently defined as follows: hydrogen, $C_1$-$C_{20}$ alkyl, phenyl, pyridyl, or heteroaromatic bases from the group of the pyridines (V), for example picoline. Preferred bases are triethylamine, 3-picoline, di-n-butylamine, n-butylamine. Particularly preferred bases are triethylamine and di-n-butylamine The process according to the invention is typically conducted between 0° C. and 200° C., preferably in the range between 20° C. and 100° C., more preferably between 40° C. and 80° C.

The reaction time is typically between 30 minutes and 48 hours, preferably between 2 and 24 hours.

The workup and isolation of the compound of the formula (I) is generally effected by cooling the reaction mixture down to a temperature range between −20° C. and 25° C., releasing any excess pressure still present and then filtering off the precipitate, washing it with the solvent used in each case and drying.

Example for Preparation of Piperidine-4-Carbothioamide Hydrochloride (I)

50 ml of ethanol, 15 g of 4-cyanopiperidine hydrochloride (102.2 mmol) and 0.52 g of triethylamine (5.1 mmol) are heated to 60° C. in a 250 ml pressure reactor. Subsequently, hydrogen sulphide is introduced into the reactor, such that there is a constant gauge pressure of 4 bar. After 5 hours, no further hydrogen sulphide is introduced, and the reaction mixture is stirred at 60° C. for a further 12 hours and then cooled down to 20° C. Excess hydrogen sulphide is discharged via a chlorine bleach scrubber, then the reaction mixture is cooled down further to 10° C. and the gas space of the reactor is purged with nitrogen for 15 minutes. The solids present in the reactor are subsequently filtered off with suction using a glass suction filter, washed once more with a little ethanol (25 ml) and dried by suction. On completion of drying at 40° C. under reduced pressure, 16.8 g (92.9 mmol, 91% of theory) of the desired piperidine-4-carbothioamide hydrochloride (I) are obtained in a purity of 99% ($^1$H NMR).

$^1$H NMR (DMSO-$d_6$, 600 MHz) δ=9.49 (1H, s), 9.37 (1H, s), 9.03 (1H, bs), 3.40 (1H, bs), 3.28 (2H, m), 2.81 (3H, m), 1.93 (2H, m), 1.82 (2H, m);

$^{13}$C NMR (DMSO-$d_6$, 150 MHz) δ=209.8, 45.7, 42.5, 28.2 ppm.

An identical reaction procedure, except using alternative bases, gives the yields listed below:

| Base | Amount (%) | Yield |
|---|---|---|
| — | — | 0% |
| Triethylamine | 5% | 91% |
| Triethylamine | 1% | 83% |
| 3-Picoline | 5% | 66% |
| Di-n-butylamine | 5% | 92% |
| n-Butylamine | 5% | 73% |

The invention claimed is:

1. A process for preparing piperidine-4-carbothioamide hydrochloride of formula (I)

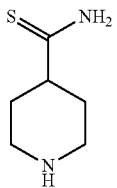
(I)

wherein said process comprises reacting 4-cyanopiperidine hydrochloride of formula (II) with

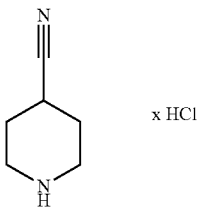
(II)

hydrogen sulfide (III)
in the presence of a catalytic amount of a base of formula (IV)

$R^1N(R^2)R^3$     (IV), in which $R^1$, $R^2$, $R^3$ are each independently hydrogen or $C_1$-$C_{20}$ alkyl,
or in the presence of a catalytic amount of a heteroaromatic base from the group of picolines (V),
wherein the catalytic amount of either the base of formula (IV) or the heteroaromatic base from the group of picolines (V) is between 0.1% and 20%, based on the amount of the piperidine-4-carbothioamide hydrochloride (I) to be produced,
and
in the presence of a solvent to give the compound of formula (I) wherein the solvent is a primary, secondary or tertiary alcohol or a mixture thereof, or a mixture of a primary, secondary and/or tertiary alcohol with one or more further solvents.

2. The process according to claim 1, wherein the base used is triethylamine, 3-picoline, di-n-butylamine or n-butylamine.

3. The process according to claim 1, wherein the base used is triethylamine.

4. The process according to claim 1, wherein the reaction is conducted in a closed reaction vessel.

5. The process according to claim 1, wherein the reaction is conducted at a reaction temperature of ≥0° C.

6. The process according to claim 1, wherein the solvent is an alcohol having 1 to 10 carbon atoms.

7. The process according to claim 1, wherein the solvent is methanol, ethanol, isopropanol, tert-butanol, i-butanol, n-butanol, cyclopentanol or cyclohexanol.

8. The process according to claim 1, wherein the reaction is conducted at a reaction temperature of from 20° C. to 100° C.

9. The process according to claim 1, wherein the reaction is conducted at a reaction temperature of from 40° C. to 80° C.

10. The process according to claim 1, wherein the base used is of formula (IV) in which $R^1$, $R^2$, $R^3$ are each independently hydrogen or $C_1$-$C_{20}$ alkyl.

11. The process according to claim 1, wherein the base used is from the group of picolines (V).

12. The process according to claim 1, wherein the base used is 3-picoline.

13. The process according to claim 1, wherein the base used is di-n-butylamine.

14. The process according to claim 1, wherein the base used is n-butylamine.

15. The process according to claim 1, wherein the catalytic amount of either the base of formula (IV) or the heteroaromatic base from the group of picolines (V) is between 1% and 5%, based on the amount of the piperidine-4-carbothioamide hydrochloride (I) to be produced.

16. The process according to claim 1, wherein the 4-cyanopiperidine hydrochloride (II) is not neutralized prior to reacting with hydrogen sulfide (III).

17. The process according to claim 1, wherein the time of reaction is between 30 minutes and 48 hours.

18. The process according to claim 1, wherein the time of reaction is between 2 and 24 hours.

19. The process according to claim 1, wherein 1.00 to 10 equivalents of hydrogen sulfide (III) are used based on the 4-cyanopiperidine hydrochloride (II).

20. The process according to claim 1, wherein 1.5 to 3 equivalents of hydrogen sulfide (III) are used based on the 4-cyanopiperidine hydrochloride (II).

* * * * *